(12) United States Patent
Krull et al.

(10) Patent No.: US 8,067,635 B2
(45) Date of Patent: Nov. 29, 2011

(54) METHOD FOR PRODUCING TERTIARY AMIDES OF ALKYLPHENYL CARBOXYLIC ACIDS

(75) Inventors: Matthias Krull, Harxheim (DE); Roman Morschhaeuser, Mainz (DE); Alexander Lerch, Gelnhausen (DE); Helmut Ritter, Wuppertal (DE); Sarah Schmitz, Duesseldorf (DE)

(73) Assignee: Clariant Finance (BVI) Limited, Tortola (VG)

( * ) Notice: Subject to any disclaimer, the term of this patent is extended or adjusted under 35 U.S.C. 154(b) by 93 days.

(21) Appl. No.: 12/444,655

(22) PCT Filed: Oct. 5, 2007

(86) PCT No.: PCT/EP2007/008679
§ 371 (c)(1),
(2), (4) Date: Jun. 9, 2009

(87) PCT Pub. No.: WO2008/043494
PCT Pub. Date: Apr. 17, 2008

(65) Prior Publication Data
US 2010/0081843 A1 Apr. 1, 2010

(30) Foreign Application Priority Data
Oct. 9, 2006 (DE) .......................... 10 2006 047 620

(51) Int. Cl.
*C07C 231/02* (2006.01)
(52) U.S. Cl. ........................................ 564/139
(58) Field of Classification Search .................... None
See application file for complete search history.

(56) References Cited

U.S. PATENT DOCUMENTS

| | | |
|---|---|---|
| 3,024,260 A | 3/1962 | Ernst |
| 3,113,026 A | 12/1963 | Sprung |
| 3,395,162 A | 7/1968 | Lamberti |
| 3,652,671 A | 3/1972 | Barron |
| 3,682,946 A | 8/1972 | Liechti |
| 4,133,833 A | 1/1979 | Hull |
| 4,582,933 A | 4/1986 | Mertens et al. |
| 4,675,319 A | 6/1987 | Nardi et al. |
| 4,859,796 A | 8/1989 | Hurtel et al. |
| 4,994,541 A | 2/1991 | Dell et al. |
| 6,017,426 A | 1/2000 | Semeria et al. |
| 2005/0272631 A1 | 12/2005 | Miracle et al. |
| 2005/0283011 A1 | 12/2005 | Hoong et al. |
| 2007/0060762 A1 | 3/2007 | Kawashima et al. |
| 2010/0010244 A1 | 1/2010 | Krull et al. |
| 2010/0032284 A1 | 2/2010 | Krull et al. |
| 2010/0076040 A1 | 3/2010 | Krull et al. |
| 2010/0116642 A1 | 5/2010 | Krull et al. |

FOREIGN PATENT DOCUMENTS

| | | |
|---|---|---|
| DE | 1139738 | 11/1962 |
| DE | 2009156 | 7/1970 |
| DE | 3209800 | 9/1983 |
| DE | 224203 | 7/1985 |
| EP | 0207901 | 1/1987 |
| EP | 0226501 | 6/1987 |
| EP | 0377177 | 7/1997 |
| EP | 0884305 | 12/1998 |
| EP | 1435364 | 7/2004 |
| WO | WO2004/072031 | 8/2004 |
| WO | WO2005/033062 | 4/2005 |
| WO | WO2005/118526 | 12/2005 |

OTHER PUBLICATIONS

Gelens et al., Tetrahedron Letters (2005), 46(21), p. 3751-3754.*
Kumar, et al., "Microwave Assisted Direct Synthesis of 2-Substituted Benzoxazoles From Carboxylic Acids Under Catalyst and Solvent-Free Conditions", Synlett, No. 9, 2005, pp. 1401-1404.
Goretzki et al., Macromol. Rapid Commun. 2004, 25, 513-516.
Gelens et al., Tetrahedron Letters 2005, 46(21), 3751-3754.
M. S. Nery, et al., "Niobium pentachloride promoted conversion of carboxylic acids to carboxamides: Synthesis of the 4-aryl-1,2,3,4-tetrahydrolsoquinollne alkaloid structures" Synthesis, (2),272-276, 2003.
Vazquez-Tato, M.P., "Microwave-Mediated Synthesis of Amides", Synlett, No. 7, 1993, p. 506.
X. Wu, et al., "Microwave Enhanced Aminocarbonylations in Water", Organic Letters, 7(15), pp. 3327-3329, 2005.
Massicot et al., Synthesis 2001 (16), 2441-2444.
Iannelli et al., Tetrahedron 2005, 61, 1509-1515.
R. Martinez-Palou, et al., "Synthesis of Long Chain 2-Alkyl-1-(2-hydroxyethyl)-2-imidazolines Under Microwave in Solvent-Free Conditions", Synlett 2003, No. 12, pp. 1847-1849.
R. Plantier-Royon, at al., "Synthesis of Functionalized Bis-Amides of L-(+)-Tartaric Acid and Application as Copper(II) Ligands", C.R. Chimie, 2004, pp. 119-123.
R.S. Hunter, "Conversion of Visual to Instrumental Measurements of Yellowness", 1981, JAOCS, May, pp. 606-612.
Synthewave 402 Manual, 2000, Prolabo, Support pp. (2) and Manual pp. 1-13 (total 15 pages).
Beilstein Substance Identification, BRN No. 6190607, 1981.
S. Schmitz, et al., "Access to Poly{N-[3-(dimethylamino)propyl](meth)acrylamide} via Microwave-Assisted Synthesis and Control of LCST-Behavior in Water", Macromolecular Rapid Communications, vol. 28, No. 21, Nov. 1, 2007, pp. 2080-2083.
H.J. Bauer, et al., Makromol. Chem., 183, 1982, pp. 2971-2976.
International Search Report for PCT/EP2007/008677 Mail dated Mar. 3, 2008.
International Search Report for PCT/EP2007/008678 Mail dated Mar. 10, 2008.
International Search Report for PCT/EP2007/008679 Mail dated Feb. 4, 2008.
International Search Report for PCT/EP2007/008680 Mail dated Feb. 15, 2008.
International Search Report for PCT/EP2007/008681 Mail dated Jan. 29, 2008.

* cited by examiner

*Primary Examiner* — Brian J Davis
(74) *Attorney, Agent, or Firm* — Tod A. Waldrop

(57) ABSTRACT

The invention relates to a method for producing tertiary amides of alkylphenyl carboxylic acids by reacting at least one secondary amine with at least one alkylphenyl carboxylic acid to form an ammonium salt, said ammonium salt being subsequently converted into the tertiary amide by means of microwave radiation.

15 Claims, No Drawings

METHOD FOR PRODUCING TERTIARY AMIDES OF ALKYLPHENYL CARBOXYLIC ACIDS

Tertiary amides of alkylphenylcarboxylic acids are a class of compounds of very great pharmacological and also industrial interest. For example, amides of alkyl-benzoic acids with secondary alkylamines find use as insect repellents.

Various methods have been developed for the preparation of amides of aromatic carboxylic acids. To date, there has been a reliance on costly and laborious preparation processes in order to achieve a yield of commercial interest. The known preparation processes require highly reactive carboxylic acid derivatives, for example acid anhydrides, acid halides, for example acid chlorides, esters, or in situ activation by the use of coupling reagents, for example N,N'-dicyclohexyl-carbodiimide, or very specific and hence expensive catalysts. Some of these preparation processes form large amounts of undesired by-products such as alcohols, acids and salts, which have to be removed from the product and disposed of. However, the residues of these assistants and by-products which remain in the products may also have some very undesired effects. For example, halide ions and also acids lead to corrosion. Some of the coupling reagents and the by-products formed by them are toxic, sensitizing or carcinogenic.

In order to increase the efficiency of syntheses and to reduce the amount of the by-products to be disposed of, there is a search for new methods to prepare tertiary amides directly from alkylphenylcarboxylic acid and secondary amine without using coupling reagents. The direct thermal condensation of alkylphenyl-carboxylic acids and secondary amines requires, however, in conventional batch processes, very long reaction times of up to several days at temperatures of often more than 300° C. and does not lead to satisfactory results, since various side reactions reduce the yield. Examples include decarboxylation of the carboxylic acid, oxidation of the amino group during the long heating and, more particularly, thermally induced degradation of the secondary amino group. The amount of by-products formed additionally entails complicated workup steps.

A more recent approach to the synthesis of amides is the microwave-supported reaction of carboxylic acids and amines to give amides. For instance, Gelens et al., Tetrahedron Letters 2005, 46(21), 3751-3754, disclose the syntheses of a multitude of amides which have been carried out with irradiation by microwaves. The reactions of carboxylic acids with electron-withdrawing substituents, for example the aryl radical (benzoic acid), require very high reaction temperatures of 250 to 300° C. and nevertheless lead only to moderate conversions. Particularly problematic reactions are those of benzoic acid with dialkylamines, which lead to tertiary amides. For instance, the reaction of benzoic acid with di(n-propyl)amine at 250° C. leads only to 10% diamide; it can be increased to 50% by increasing the reaction temperature. The corresponding reaction with dibenzylamine leads at 250° C. to a yield of dibenzylamide of only 25%; further temperature increase to 300° C. leads principally to decarboxylation of the benzoic acid used and not to the tertiary amide. Such conversions are much too low for industrial processes. The decarboxylation is particularly disadvantageous from commercial and also ecological aspects, since the aromatic hydrocarbons formed cannot be recycled into the process and must instead be disposed of.

It was an object of the present invention to find a process for preparing tertiary amides of alkylphenylcarboxylic acids, in which alkylphenylcarboxylic acid and secondary amine can be converted directly and in high, i.e. up to quantitative, yields to the tertiary amide. In addition, only minor amounts, if any, of by-products such as secondary amides and/or decarboxylated carboxylic acids should occur.

It has been found that, surprisingly, tertiary amides of alkylphenylcarboxylic acids can be prepared in high yields and with high purity by directly reacting secondary amines with alkylphenylcarboxylic acids by irradiating with microwaves. Surprisingly, in the case of substitution of the aromatic system by at least one alkyl group, virtually no decarboxylation of the arylcarboxylic acid occurs. Moreover, only minor elimination at the amino group takes place and the reaction products are virtually colorless.

The invention provides a process for preparing tertiary amides of alkylphenyl-carboxylic acids by reacting at least one secondary amine with at least one alkyl-phenylcarboxylic acid to give an ammonium salt, and then converting this ammonium salt further under microwave irradiation to the tertiary amide.

Tertiary amides are understood to mean amides whose amide nitrogen atom bears two hydrocarbon radicals.

Alkylphenylcarboxylic acids are understood to mean those acids which comprise at least one carboxyl group and at least one alkyl radical bonded directly to an aromatic system having (4n+2) π electrons in which n is a natural number and is preferably 1, 2, 3, 4 or 5. Examples of such aromatic systems are benzene, naphthalene and phenanthrene. As well as carboxyl and alkyl groups, the aromatic system may bear one or more, for example one, two, three or more, identical or different further substituents. Suitable further substituents are, for example, halogenated alkyl radicals, and hydroxyl, hydroxyalkyl, alkoxy, halogen, cyano, nitrile, nitro and/or sulfonic acid groups. These may be bonded to any position of the aromatic system.

The process according to the invention is more preferably employed for the amidation of aromatic carboxylic acids which comprise an aromatic system which has (4n+2) π electrons and bears a carboxyl group and an alkyl radical having 1 to 20 carbon atoms, and in which n is an integer from 1 to 4.

The process is particularly advantageous in the amidation of alkylbenzoic acids which bear at least one alkyl radical having 1 to 20 carbon atoms and especially 1 to 12 carbon atoms, for example 1 to 4 carbon atoms. The process according to the invention is particularly suitable for the amidation of o-toluic acid, m-toluic acid, p-toluic acid, o-ethylbenzoic acid, m-ethylbenzoic acid, p-ethylbenzoic acid, o-propylbenzoic acid, m-propylbenzoic acid, p-propylbenzoic acid and 3,4-dimethylbenzoic acid.

Secondary amines suitable in accordance with the invention possess at least one amino group which bears two hydrocarbon radicals and a proton to form the amide bond.

Preferred amines are of the formula

HNR$^1$R$^2$ in which R$^1$ and R$^2$ are each independently $C_1$-$C_{24}$-alkyl, $C_5$-$C_{12}$-cycloalkyl or $C_7$-$C_{30}$-aralkyl.

R$^1$ and R$^2$ are preferably each independently $C_1$-$C_{12}$-alkyl and especially $C_1$-$C_6$-alkyl. The alkyl radicals may be linear or branched. The R$^1$ and R$^2$ radicals may be substituted by heteroatoms, for example O and/or S, and/or substituents containing such heteroatoms. However, they preferably do not contain more than 1 heteroatom per 2 carbon atoms. Thus, in a further preferred embodiment, R$^1$ and/or R$^2$ are each independently polyoxyalkylene radicals of the formula

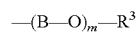
—(B—O)$_m$—R$^3$ in which

B is a linear or branched $C_2$-$C_4$-alkylene radical, especially a group of the formula —$CH_2$—$CH_2$— and/or —$CH(CH_3)$—$CH_2$—, m is from 1 to 100, preferably 2 to 20, and $R^3$ is hydrogen, an alkyl radical having 1 to 20 carbon atoms, a cycloalkyl radical having 5 to 12 ring atoms, an aryl radical having 6 to 12 ring atoms, an aralkyl radical having 7 to 30 carbon atoms, a heteroaryl radical having 5 to 12 ring atoms or a heteroaralkyl radical having 6 to 12 carbon atoms.

Araliphatic radicals particularly suitable as $R^1$ and/or $R^2$ include ring systems which have at least 5 ring members and are bonded to the nitrogen via a $C_1$-$C_6$-alkyl radical. They may contain heteroatoms such as S, O and N. The aromatic and also the araliphatic radicals may bear further substituents, for example alkyl radicals, halogen atoms, halogenated alkyl radicals, and nitro, cyano, nitrile, hydroxyl and/or hydroxyalkyl groups.

Particularly preferred $R^1$ and/or $R^2$ are lower alkyl radicals, for example methyl, ethyl, n-propyl, isopropyl, n-butyl, isobutyl or tert-butyl. In particular, $R^1$ and $R^2$ are both ethyl.

Examples of suitable amines are dimethylamine, diethylamine, dipropylamine, dibutylamine, methylethylamine, dioctylamine, didecylamine, ditetradecylamine, dihexadecylamine, dioctadecylamine, and mixtures thereof.

The process is especially suitable for preparing N,N-diethyl-m-toluamide.

In the process according to the invention, alkylphenylcarboxylic acid and amine can be reacted with one another in any desired ratios. Particularly suitable molar ratios between alkylphenylcarboxylic acid and secondary amine are 10:1 to 1:100, preferably 2:1 to 1:2, especially 1.0:1.2 to 1.2:1.0 and more particularly equimolar.

In many cases, it has been found to be advantageous to work with an excess of secondary amine, i.e. molar ratios of amine to alkylphenylcarboxylic acid, of at least 1.01:1.00, especially between 1.05:1.00 and 100:1, for example between 1.1:1.0 and 10:1. This converts the acid virtually quantitatively to the tertiary amide. This process is particularly advantageous when the secondary amine used is volatile. "Volatile" means here that the amine has a boiling point at standard pressure of preferably below 200° C. and especially below 150° C., for example below 100° C., and can thus be removed from the amide by distillation.

The amides are prepared by converting the alkylphenylcarboxylic acid and the tertiary amine to the ammonium salt and then irradiating the salt with microwaves. The ammonium salt is preferably generated in situ and not isolated. The temperature rise caused by the microwave irradiation is preferably limited to a maximum of 330° C. by regulating the microwave intensity and/or cooling the reaction vessel. It has been found to be particularly useful to perform the conversion at temperatures between 200 and 300° C., for example at temperatures between 220 and 270° C.

The duration of the microwave irradiation depends on various factors, such as the reaction volume, the geometry of the reaction chamber and the desired conversion. Typically, the microwave irradiation is undertaken over a period of less than 30 minutes, preferably between 0.01 second and 15 minutes, more preferably between 0.1 second and 10 minutes and especially between 1 second and 5 minutes, for example between 5 seconds and 2 minutes. The intensity (power) of the microwave radiation is adjusted such that the reaction mixture reaches the desired reaction temperature within a minimum time. In a further preferred embodiment of the process according to the invention, it has been found to be useful to heat the ammonium salt actually before commencement of microwave irradiation, which can be accomplished, among other ways, by utilizing the heat of reaction released in the formation of the ammonium salt. It has been found to be particularly useful to heat the ammonium salt to temperatures between 40 and 200° C., but preferably to temperatures below the boiling point of the system. To subsequently maintain the temperature, the reaction mixture can be irradiated further with reduced and/or pulsed power. To maintain the maximum temperature with simultaneously maximum microwave incidence, it has been found to be useful to cool the reaction mixture, for example, by means of a cooling jacket, cooling tubes present in the reaction chamber through intermittent cooling between different irradiation zones, and/or by evaporative cooling by means of external heat exchangers. In a preferred embodiment, the reaction product is cooled directly after the microwave irradiation has ended as rapidly as possible to temperatures below 120° C., preferably below 100° C. and especially below 50° C.

Preference is given to performing the reaction at pressures between 0.1 and 200 bar and especially between 1 bar (atmospheric pressure) and 50 bar. It has been found to be particularly useful to work in closed vessels in which operation is effected above the boiling point of the reactants and/or products, of the solvent which may be present and/or above the water of reaction formed during the reaction. Typically, the pressure which is established owing to the heating of the reaction mixture is sufficient for successful performance of the process according to the invention. However, it is also possible to work under elevated pressure and/or with application of a pressure profile. In a further preferred variant of the process according to the invention, atmospheric pressure, as established, for example, in the open vessel, is employed.

To prevent side reactions and to prepare very pure products, it has been found to be useful to perform the process according to the invention in the presence of an inert protective gas, for example nitrogen, argon or helium.

In a preferred embodiment, the reaction is accelerated or completed by working in the presence of dehydrating catalysts. Preference is given to working in the presence of an acidic inorganic, organometallic or organic catalyst, or mixtures of a plurality of these catalysts.

Examples of acidic inorganic catalysts in the context of the invention include boric acid, sulfuric acid, phosphoric acid, polyphosphoric acid, phosphonic acid, hypo-phosphorous acid, aluminum sulfate hydrate, alum, acidic silica, acidic aluminum hydroxide and zinc chloride. It has been found to be particularly useful to use boric acid, phosphoric acid, polyphosphoric acid or zinc chloride.

In addition and with particular preference, aluminum compounds of the formula $Al(OR^5)_3$ and especially titanates of the formula $Ti(OR^5)_4$ are used as acidic inorganic catalysts. The $R^5$ radicals may each be the same or different and may each independently be selected from $C_1$-$C_{10}$-alkyl radicals, for example methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, sec-hexyl, n-heptyl, n-octyl, 2-ethylhexyl, n-nonyl or n-decyl, $C_3$-$C_{12}$-cycloalkyl radicals, for example cyclopropyl, cyclobutyl, cyclopentyl, cyclohexyl, cycloheptyl, cyclooctyl, cyclononyl, cyclodecyl, cycloundecyl and cyclododecyl; preference is given to cyclopentyl, cyclohexyl and cycloheptyl. The $R^5$ radicals in $Al(OR^5)_3$ or $Ti(OR^5)_4$ are preferably each the same and are selected from isopropyl, butyl and 2-ethylhexyl.

Preferred acidic organometallic catalysts are, for example, selected from dialkyltin oxides $(R^5)_2SnO$ where $R^5$ is as defined above. A particularly preferred representative of acidic organometallic catalysts is di-n-butyltin oxide, which is commercially available as so-called oxo-tin or as Fascat® brands.

Preferred acidic organic catalysts are acidic organic compounds with, for example, phosphate groups, sulfonic acid groups, sulfate groups or phosphonic acid groups. Particularly preferred sulfonic acids contain at least one sulfonic acid group and at least one saturated or unsaturated, linear, branched and/or cyclic hydrocarbon radical having 1 to 40 carbon atoms and preferably having 3 to 24 carbon atoms. Especially preferred are aromatic sulfonic acids, especially alkylaromatic mono-sulfonic acids having one or more $C_1$-$C_{28}$-alkyl radicals and especially those having $C_3$-$C_{22}$-alkyl radicals. Suitable examples are methanesulfonic acid, butane-sulfonic acid, benzenesulfonic acid, p-toluenesulfonic acid, xylenesulfonic acid, 2-mesitylenesulfonic acid, 4-ethylbenzenesulfonic acid, isopropylbenzenesulfonic acid, 4-butylbenzenesulfonic acid, 4-octylbenzenesulfonic acid; dodecylbenzene-sulfonic acid, didodecylbenzenesulfonic acid, naphthalenesulfonic acid. It is also possible to use acidic ion exchangers as acidic organic catalysts, for example sulfonic acid group-containing poly(styrene) resins which have been crosslinked with about 2 mol % of divinylbenzene.

Particularly preferred for the performance of the process according to the invention are boric acid, phosphoric acid, polyphosphoric acid and polystyrenesulfonic acids. Especially preferred are titanates of the formula $Ti(OR^5)_4$ and especially titanium tetrabutoxide and titanium tetraisopropoxide.

If it is desired to use acidic inorganic, organometallic or organic catalysts, 0.01 to 10.0% by weight, preferably 0.05 to 5.0% by weight, for example 0.1 to 2.0% by weight, of catalyst is used in accordance with the invention, based on the mass of reactants used. A particularly preferred embodiment works without catalyst.

In a further preferred embodiment, the microwave irradiation is performed in the presence of acidic solid catalysts. The solid catalyst is suspended in the ammonium salt which has optionally been admixed with solvent, or, especially in continuous processes, the ammonium salt optionally admixed with solvent is passed over a fixed bed catalyst and exposed to the microwave radiation. Suitable solid catalysts are, for example, zeolites, silica gel and montmorillonite, or else (partly) crosslinked polystyrenesulfonic acids, which may optionally be impregnated with catalytically active metal salts. Suitable acidic ion exchangers which are based on crosslinked polystyrenesulfonic acids and can be used as solid-phase catalysts are obtainable, for example, from Rohm&Haas under the name Amberlyst®.

It has been found to be useful to work in the presence of solvents in order, for example, to lower the viscosity of the reaction medium, to fluidize the reaction mixture if it is heterogeneous, and/or to improve the heat removal, for example by means of evaporative cooling. For this purpose, it is possible in principle to use all solvents which are inert under the reaction conditions employed and do not react with the reactants or the products formed. An important factor in the selection of suitable solvents is their polarity, which determines firstly the solution properties and secondly the degree of interaction with microwave radiation. A particularly important factor in the selection of suitable solvents is their dielectric loss $\in$". The dielectric loss $\in$" describes the proportion of microwave radiation which is converted to heat when a substance interacts with microwave radiation. The latter value has been found to be a particularly important criterion for the suitability of a solvent for the performance of the process according to the invention. It has been found to be particularly useful to work in solvents which exhibit minimum microwave absorption and thus make only a small contribution to the heating of the reaction system. Solvents preferred for the process according to the invention possess a dielectric loss $\in$", measured at room temperature and 2450 MHz, of less than 10 and preferably less than 1, for example less than 0.5. An overview of the dielectric loss of different solvents can be found, for example, in "Microwave Synthesis" by B. L. Hayes, CEM Publishing 2002. Suitable solvents for the process according to the invention are especially solvents with $\in$" values below 10, such as N-methylpyrrolidone, N,N-dimethylformamide or acetone, and especially solvents with $\in$" values below 1. Examples of particularly preferred solvents with $\in$" values below 1 are aromatic and/or aliphatic hydrocarbons, for example toluene, xylene, ethylbenzene, tetralin, hexane, cyclohexane, decane, pentadecane, decalin, and commercial hydrocarbon mixtures such as petroleum fractions, kerosene, Solvent Naphtha, ®Shellsol AB, ®Solvesso 150, ®Solvesso 200, ®Exxsol, ®Isopar and ®Shellsol types. Solvent mixtures which have $\in$" values preferably below 10 and especially below 1 are equally preferred for the performance of the process according to the invention. In principle, the process according to the invention is also possible in solvents with $\in$" values of 10 and higher, but this requires particular measures for complying with the maximum temperature and often leads to reduced yields. When working in the presence of solvents, the proportion thereof in the reaction mixture is preferably between 2 and 95% by weight, especially between 5 and 90% by weight and in particular between 10 and 75% by weight, for example between 30 and 60% by weight. Particular preference is given to performing the reaction without solvent.

The microwave irradiation is typically performed in units which possess a reaction chamber composed of a material very substantially transparent to microwaves, into which microwave radiation generated in a microwave generator is injected through suitable antenna systems. Microwave generators, for example the magnetron and the klystron, are known to those skilled in the art.

Microwaves refer to electromagnetic rays having a wavelength between about 1 cm and 1 m and frequencies between about 300 MHz and 30 GHz. This frequency range is suitable in principle for the process according to the invention. Preference is given to using, for the process according to the invention, microwave radiation with the frequencies approved for industrial, scientific and medical applications of 915 MHz, 2.45 GHz, 5.8 GHz or 27.12 GHz. It is possible to work either in monomode or quasi-monomode, or else in multimode. In the case of monomode, which places high demands on the geometry and size of the apparatus and reaction chamber, a very high energy density is generated by a standing wave, especially at the maximum thereof. In multimode, in contrast, the entire reaction chamber is irradiated substantially homogeneously, which enables, for example, greater reaction volumes.

The microwave power to be injected into the reaction vessel for the performance of the process according to the invention is dependent especially on the geometry of the reaction chamber and hence of the reaction volume, and on the duration of the irradiation required. It is typically between 100 W and several hundred kW, and especially between 200 W and 100 kW, for example between 500 W and 70 kW. It can be applied at one or more sites in the reactor. It can be generated by means of one or more microwave generators.

The reaction can be carried out batchwise or preferably continuously in a flow tube, for example. It can additionally be performed in semibatchwise processes, for example continuous stirred reactors or cascade reactors. In a preferred embodiment, the reaction is performed in a closed vessel, in which case the condensate which forms and if appropriate reactants and, where present, solvents lead to a pressure buildup. After the reaction has ended, the elevated pressure can be used by decompression to volatilize and remove water of reaction, and if appropriate solvents and excess reactants, and/or cool the reaction product. In a further embodiment, the water of reaction formed, after cooling and/or decompression, is removed by customary processes, for example phase separation, distillation and/or absorption. The process according to the invention can be effected equally successfully in an open vessel with evaporative cooling and/or separation of the water of reaction.

In a preferred embodiment, the process according to the invention is performed in a batchwise microwave reactor. The microwave irradiation is undertaken in a stirred vessel. To remove excess heat, cooling elements are preferably present in the reaction vessel, for example cooling fingers or cooling coils, or reflux condensers flanged onto the reaction vessel for evaporative cooling of the reaction medium. For the irradiation of relatively large reaction volumes, the microwave here is preferably operated in multimode. The batchwise embodiment of the process according to the invention allows, through variation of the microwave power, rapid or else slow heating rates, and especially the maintenance of the temperature over prolonged periods, for example several hours. The reactants and any solvents and further assistants can be initially charged in the reaction vessel before commencement of the microwave irradiation. They preferably have temperatures below 100° C., for example between 10 and 50° C. In a preferred embodiment, the reactants or portions thereof are not added to the reaction vessel until during the irradiation with microwaves. In a further preferred embodiment, the batchwise microwave reactor is operated with continuous supply of reactants and continuous discharge of reaction mixture in the form of a semibatchwise or cascade reactor.

In a particularly preferred embodiment, the process according to the invention is performed in a continuous microwave reactor. To this end, the reaction mixture is conducted through a pressure-resistant reaction tube which is inert toward the reactants, is very substantially transparent to microwaves and is built into a microwave oven. This reaction tube preferably has a diameter of one millimeter to approx. 50 cm, especially between 2 mm and 35 cm, for example between 5 mm and 15 cm. Reaction tubes are understood here to mean vessels whose ratio of length to diameter is greater than 5, preferably between 10 and 100,000, more preferably between 20 and 10,000, for example between 30 and 1000. In a specific embodiment, the reaction tube is configured in the form of a jacketed tube through whose interior and exterior the reaction mixture can be conducted successively in countercurrent, in order, for example, to increase the thermal conduction and energy efficiency of the process. The length of the reaction tube is understood to mean the total distance through which the reaction mixture flows. Over its length, the reaction tube is surrounded by at least one microwave radiator, but preferably by more than one, for example two, three, four, five, six, seven, eight or more microwave radiators. The microwaves are preferably injected through the tube jacket. In a further preferred embodiment, the microwaves are injected by means of at least one antenna via the tube ends. The reaction tube is typically provided at the inlet with a metering pump and a manometer, and at the outlet with a pressure-retaining valve and a heat exchanger. The amine and alkylphenylcarboxylic acid reactants, each independently optionally diluted with solvent, are preferably not mixed until shortly before entry into the reaction tube. Additionally preferably, the reactants are supplied to the process according to the invention in liquid form at temperatures below 100° C., for example between 10° C. and 50° C. To this end, it is possible to use relatively high-melting reactants, for example, in the molten state or admixed with solvent.

Variation of tube cross section, length of the irradiation zone (this is understood to mean the proportion of the reaction tube in which the reaction mixture is exposed to microwave irradiation), flow rate, geometry of the microwave radiators, the microwave power injected and the temperature attained as a result are used to adjust the reaction conditions such that the maximum reaction temperature is attained as rapidly as possible and the residence time at maximum temperature remains sufficiently short that as low as possible a level of side reactions or further reactions occurs. Preference is given to operating the continuous microwave reactor in monomode or quasi-monomode. The residence time in the reaction tube is generally below 30 minutes, preferably between 0.01 second and 15 minutes, preferably between 0.1 second and 5 minutes, for example between 1 second and 3 minutes. To complete the reaction, if appropriate after intermediate cooling, the reaction mixture can pass through the reactor more than once. It has been found to be particularly useful when the reaction product, immediately after leaving the reaction tube, is cooled, for example by jacket cooling or decompression.

It was particularly surprising that, in spite of the only very short residence time of the ammonium salt in the microwave field in the flow tube with continuous flow, such a substantial amidation takes place without formation of significant amounts of by-products. In the case of a corresponding reaction of these ammonium salts in a flow tube with thermal jacket heating, extremely high wall temperatures are required to achieve suitable reaction temperatures, and lead to the formation of colored species, but bring about virtually no amide formation.

To complete the reaction, it has been found to be useful in many cases to dry the resulting crude product to remove water of reaction and to expose it again to microwave irradiation. In a further preferred embodiment, it has been found to be useful to recycle unconverted reactants into the process according to the invention after removal from the reaction product, which leads to a virtually quantitative conversion of the reactants used and especially of the alkylphenylcarboxylic acid.

Typically, tertiary amides prepared via the inventive route are obtained in a purity sufficient for further use. For specific requirements, they can, however, be purified further by customary purification processes such as distillation, recrystallization, filtration or chromatographic processes.

The process according to the invention allows a very rapid and inexpensive preparation of tertiary amides of alkylphenylcarboxylic acids in high yields and with high purity. At the same time, no significant amounts of by-products are obtained. The products prepared by the process according to the invention are additionally virtually colorless, i.e. they possess iodine color numbers of less than 5 and often less than 2, for example between 0.1 and 1.5. Products prepared by thermal condensation in an autoclave, in contrast, typically have iodine color numbers above 30 or often cannot be measured at all. Therefore, typically no workup or reprocessing steps are required for products prepared by the process according to the invention. A particularly surprising observation was that alkylphenylcarboxylic acids do not exhibit any noticeable decarboxylation under the conditions of the process according to the invention. Such rapid and selective reactions are unachievable by conventional methods and were also not to be expected through heating to high temperatures alone. The tertiary amides, prepared in accordance with the invention, of alkylphenylcarboxylic acids are suitable especially as insect repellents. Since the tertiary amides prepared by the process according to the invention, by virtue of the process, do not contain any residues of coupling reagents or conversion products thereof, they can also be used without any problem in toxicologically sensitive areas, for example cosmetic and pharmaceutical formulations.

EXAMPLES

The reactions under microwave irradiation were effected in a CEM "Discover" single-mode microwave reactor at a frequency of 2.45 GHz. The reaction vessels were cooled by means of compressed air. Owing to the pressure conditions in the reaction vessels, the temperature had to be measured by means of an IR sensor at the base of the cuvette. Comparative tests with a glass fiber optic immersed into the reaction mixture found that the temperature in the reaction medium, within the temperature range relevant here, is about 50 to 80° C. above the temperature measured at the base of the cuvette with the IR sensor.

The batchwise reactions were effected in closed, pressure-resistant glass cuvettes with a volume of 8 ml with magnetic stirring. Continuous reactions were effected in pressure-resistant cylindrical glass cuvettes configured as a jacketed tube (approx. 10×1.5 cm; reaction volume approx. 15 ml) with an internal inlet tube ending above the base of the cuvette, and product outlet at the upper end of the cuvette. The pressure which built up during the reaction was limited to a maximum of 20 bar by means of a pressure-retaining valve and released into a reservoir. The ammonium salt was pumped into the cuvette through the inlet tube, and the residence time in the irradiation zone was adjusted to about 1 minute by modifying the pump output.

The products were analyzed by means of $^1$H NMR spectroscopy at 500 MHz in pyridine-$d_5$ or by means of GC-MS. The detection limit for aromatic hydrocarbons was approx. 1%. Water determinations were effected by means of Karl-Fischer titration.

Example 1

Preparation of N,N-diethyl-m-toluamide 1 g of diethylamine was admixed slowly with an equimolar amount (1.9 g) of m-toluic acid with cooling. After the exothermicity had abated, the ammonium salt thus obtained was exposed to microwave irradiation of 150 W in a closed cuvette for 5 minutes with maximum cooling performance. A temperature of 160° C. measured by means of an IR sensor was attained; the pressure rose to about 14 bar. Subsequently, the reaction mixture was cooled to 30° C. within 2 minutes.

The resulting crude product contained, as main components, 66% N,N-diethyl-m-toluamide, 2% N-ethyl-m-toluamide, 6% water and unconverted reactants. After the reaction mixture had been dried over molecular sieve, irradiated again with 150 W microwaves for one minute and dried over molecular sieve, a 92% conversion of the m-toluic acid to N,N-diethyl-m-toluamide was achieved. No toluene was detectable as a thermal cleavage product. The iodine color number was 3.

Example 2

Preparation of N,N-diethyl-m-toluamide with Catalysis by Boric Acid/p-toluenesulfonic Acid 0.53 g of diethylamine were admixed slowly with an equimolar amount (1.0 g) of m-toluic acid with cooling. After the exothermicity had abated, the ammonium salt thus obtained was admixed with 15.6 mg of boric acid and 15 mg of p-toluene-sulfonic acid, and exposed to microwave irradiation of 75 W with maximum cooling performance for 5 minutes. A temperature of 200° C. measured by means of an IR sensor was attained; the pressure rose to 20 bar. Subsequently, the reaction mixture was cooled to 30° C. within 2 minutes.

The resulting crude product contained, as main components, 75% N,N-diethyl-m-toluamide and 8% N-ethyl-m-toluamide and unconverted reactants, and also 6.5% water. No toluene was detectable as a thermal cleavage product. The iodine color number was 4.

Example 3

Preparation of N,N-diethyl-m-toluamide with Catalysis by Titanium Tetrabutoxide 2 g of diethylamine were admixed slowly with 1 g of m-toluic acid with cooling. After the exothermicity had abated, the ammonium salt thus obtained was admixed with 30 mg of titanium tetrabutoxide and exposed to microwave irradiation of 150 W in a closed cuvette with maximum cooling performance for 2 minutes. A temperature of 200° C. measured by means of an IR sensor was attained; the pressure rose to 20 bar. Subsequently, the reaction mixture was cooled to 30° C. within 2 minutes.

In the resulting crude product, 81% of the toluic acid had been converted to N,N-diethyl-m-toluamide and a further 9% to N-ethyl-m-toluamide. After removal of the water of reaction and reirradiation, and subsequent distillative removal of water and excess diethylamine, 90% N,N-diethyl-m-toluamide was obtained. No toluene was detectable as a thermal cleavage product. The iodine color number of the resulting product was 4.

Example 4

Preparation of N,N-dihexyl-m-toluamide with Excess Dihexylamine 2.5 g of dihexylamine were admixed slowly with 1 g of m-toluic acid with cooling and stirring. After the exothermicity had abated, the solution of the ammonium salt thus obtained was exposed to microwave irradiation of 100 W with maximum cooling performance in a closed cuvette for 7 minutes. A temperature of 190° C. measured by means of an IR sensor was attained at a pressure of 16 bar. Subsequently, the reaction mixture was cooled to 30° C. within 2 minutes.

In the crude product thus obtained, 50% of the toluic acid had been converted to N,N-dihexyl-m-toluamide. After drying over molecular sieve, it was reirradiated with microwaves for 5 minutes. After excess dihexylamine and water of reaction had been distilled off, 77% N,N-dihexyl-m-toluamide (based on the m-toluic acid used) was obtained. No toluene was detectable as a thermal cleavage product. The iodine color number of the resulting product was 3.

Example 5

Continuous Preparation of N,N-diethyl-m-toluamide 100 g of diethylamine were admixed slowly with 136 g of m-toluic acid with cooling and stirring. After the exothermicity had abated, the ammonium salt thus obtained was pumped continuously through the glass cuvette mounted in the microwave cavity via the base inlet. The delivery output of the pump was adjusted such that the residence time in the cuvette and hence in the irradiation zone was about 10 seconds. Maximum cooling performance was employed with a microwave power of 300 W, and a temperature of 150° C. measured by means of an IR sensor was attained. After leaving the glass cuvette, the reaction mixture was cooled to 30° C. by means of a short Liebig condenser.

The crude product contained a yield of 56% N,N-diethyl-m-toluamide based on the m-toluic acid used. After removal of the water of reaction, another passage through the above process and distillative removal of excess diethylamine and water of reaction, a conversion of 79% N,N-diethyl-m-toluamide based on the m-toluic acid used was obtained. No toluene was detectable as a thermal cleavage product. The iodine color number of the resulting product was 1.

Example 6

Continuous Preparation of N,N-diethyl-m-toluamide 73 g of diethylamine (1 mol) were admixed slowly with 136 g of m-toluic acid (1 mol) with cooling and stirring. After the exothermicity had abated, the ammonium salt thus obtained was pumped continuously through the glass cuvette mounted in the microwave cavity via the base inlet. The delivery output of the pump was adjusted such that the residence time in the cuvette and hence in the irradiation zone was about 100 seconds. Maximum cooling performance was employed at a microwave power of 500 W, and a temperature of 200° C. measured by means of an IR sensor was attained. After leaving the glass cuvette, the reaction mixture was cooled to RT by means of a short Liebig condenser.

The crude product contained a yield of 75% N,N-diethyl-m-toluamide based on the m-toluic acid used. No toluene was detectable as a thermal cleavage product. After removal of the water of reaction and another passage through the above process, a conversion of 88% N,N-diethyl-m-toluamide based on the m-toluic acid used was obtained. The iodine color number of the resulting product was 1.

Example 7

Preparation of N,N-diethylbenzamide (Comparative 1)

2 g of diethylamine were admixed slowly with 1 g of benzoic acid with cooling. After the exothermicity had abated, the ammonium salt thus obtained was exposed to microwave irradiation of 200 W with maximum cooling power in a closed cuvette for 5 minutes. A temperature of 230° C. measured by means of an IR sensor was attained; the pressure rose to 20 bar. Subsequently, the reaction mixture was cooled to 30° C. within 2 minutes.

In the crude product, 42% of the benzoic acid used had been converted to N,N-diethylbenzamide, and a further 15% to N-ethylbenzamide. In addition, 11% benzene were present in the crude product, which originates from the thermal decarboxylation of the benzoic acid used.

Example 8

Continuous Thermal Reaction of m-toluic Acid and Diethylamine (Comparative 2)

73 g of diethylamine (1 mol) were admixed slowly with 136 g of m-toluic acid (1 mol) with cooling and stirring. After the exothermicity had abated, the ammonium salt thus obtained was pumped continuously through the pressure-resistant glass cuvette present in an oil bath at 300° C. via the base inlet. The delivery output of the pump was adjusted such that the residence time of the reactants in the cuvette and hence in the reaction zone was about 85 seconds. A temperature measurement was undertaken at the overflow of the cuvette. The maximum temperatures observed here were 220° C. After leaving the glass cuvette, the reaction mixture was cooled to RT by means of a short Liebig condenser.

The reaction mixture thus obtained contained less than 2 mol % of N,N-diethyl-m-toluamide. The iodine color number was 35.

The invention claimed is:

1. A process for preparing a tertiary amide of an alkylphenylcarboxylic acid comprising the steps of reacting at least one secondary amine with at least one alkylphenylcarboxylic acid to give an ammonium salt, and subsequently converting this ammonium salt further under microwave irradiation to the tertiary amide.

2. The process as claimed in claim 1, wherein the alkylphenylcarboxylic acid bears at least one $C_1$- to $C_{20}$-alkyl radical.

3. The process as claimed in claim 1, wherein the alkylphenylcarboxylic acid is selected from the group consisting of: o-toluic acid, m-toluic acid, p-toluic acid, o-ethylbenzoic acid, m-ethylbenzoic acid, p-ethylbenzoic acid, o-propylbenzoic acid, m-propylbenzoic acid, p-propylbenzoic acid and 3,4-dimethylbenzoic acid.

4. The process as claimed in claim 1, wherein the amine is of the formula $$HNR^1R^2$$ 

wherein $R^1$ and $R^2$ are each independently $C_1$-$C_{24}$-alkyl, $C_5$-$C_{12}$-cycloalkyl or $C_7$-$C_{30}$-aralkyl, or are each polyoxyalkylene radicals of the formula $$-(B-O)_m-R^3$$ 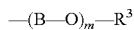

wherein
B is a linear or branched $C_2$-$C_4$-alkylene radical,
m is from 1 to 100, and
$R^3$ is hydrogen, an alkyl radical having 1 to 20 carbon atoms, a cycloalkyl radical having 5 to 12 ring atoms, an aryl radical having 6 to 12 ring atoms, an aralkyl radical having 7 to 30 carbon atoms, a heteroaryl radical having 5 to 12 ring atoms or a heteroaralkyl radical having 6 to 12 carbon atoms.

5. The process as claimed in claim 1, wherein the microwave irradiation is performed in the presence of a dehydrating catalyst.

6. The process as claimed in claim 1, performed in the presence of a solvent.

7. The process as claimed in claim 6, wherein the solvent has a dielectric loss value of less than 10.

8. The process as claimed in claim 1, wherein the reaction temperature is below 330° C.

9. The process as claimed in claim 1, wherein the reaction is performed at a pressure between 0.1 and 200 bar.

10. The process as claimed in claim 1, wherein the reaction is effected continuously by irradiating with microwaves in a reaction tube through which the ammonium salt flows.

11. The process as claimed in claim 10, wherein the reaction tube consists of a nonmetallic microwave-transparent material.

12. The process as claimed in claim 10, wherein the residence time of the reaction mixture in the reaction tube is less than 30 minutes.

13. The process as claimed in claim 10, wherein the reaction tube has a ratio of length to diameter of at least 5.

14. The process as claimed in claim 4, wherein B is a group of the formula —$CH_2$—$CH_2$— and/or —$CH(CH_3)$—$CH_2$—.

15. The process as claimed in claim 4, wherein m is from 2 to 20.

* * * * *